(12) United States Patent
Insler et al.

(10) Patent No.: US 10,874,358 B2
(45) Date of Patent: Dec. 29, 2020

(54) METHOD AND DEVICE FOR AUTOMATIC IDENTIFICATION OF AN OPIOID OVERDOSE AND INJECTION OF AN OPIOID RECEPTOR ANTAGONIST

(71) Applicants: Joseph Insler, Westwood, MA (US); Suzanne Insler, Westwood, MA (US)

(72) Inventors: Joseph Insler, Westwood, MA (US); Suzanne Insler, Westwood, MA (US)

( * ) Notice: Subject to any disclaimer, the term of this patent is extended or adjusted under 35 U.S.C. 154(b) by 799 days.

(21) Appl. No.: 15/388,695

(22) Filed: Dec. 22, 2016

(65) Prior Publication Data

US 2017/0172522 A1    Jun. 22, 2017

Related U.S. Application Data

(60) Provisional application No. 62/270,869, filed on Dec. 22, 2015.

(51) Int. Cl.
*A61B 5/00* (2006.01)
*A61B 5/0205* (2006.01)
(Continued)

(52) U.S. Cl.
CPC ............ *A61B 5/746* (2013.01); *A61B 5/0002* (2013.01); *A61B 5/02055* (2013.01); *A61B 5/1112* (2013.01); *A61B 5/14551* (2013.01); *A61B 5/4839* (2013.01); *A61B 5/4845* (2013.01); *A61B 5/6824* (2013.01); *A61B 5/6828* (2013.01); *A61B 5/6829* (2013.01); *A61B 5/6831* (2013.01); *A61B 5/7405* (2013.01); *A61B 5/7455* (2013.01); *A61K 31/485* (2013.01); *A61M 5/1452* (2013.01); *A61M 5/14244* (2013.01); *A61M 5/1723* (2013.01); *A61M 5/20* (2013.01); *A61B 5/0022* (2013.01); *A61B 5/021* (2013.01); *A61B 5/02416* (2013.01);
(Continued)

(58) Field of Classification Search
CPC .... A61B 5/746; A61B 5/4845; A61M 5/1723; A61M 2205/3303; A61M 5/14244; A61M 5/14248; A61M 2005/14252; A61M 5/16836; A61M 2005/1726; A61M 2005/206
USPC ......................................... 600/481, 484, 529
See application file for complete search history.

(56) References Cited

U.S. PATENT DOCUMENTS

| 4,777,962 A | * | 10/1988 | Watson ................ | A61B 5/1135 600/529 |
| 2012/0212339 A1 | * | 8/2012 | Goldblatt ............. | G08B 25/016 340/539.11 |

(Continued)

*Primary Examiner* — Tiffany Legette
*Assistant Examiner* — William R Frehe
(74) *Attorney, Agent, or Firm* — Arent Fox LLP (57) ABSTRACT

A method for detecting the need for providing assistance to an individual suspected of overdosing on an opiate is provided. The method includes using a wearable device for continuous or intermittent monitoring of one or more physiological parameters of the individual. If the level of one of the one or more physiological parameters exceeds a threshold level specific to that parameter, an alarm is triggered. If the alarm is not aborted, an alert is transmitted to one or more emergency contacts conveying that the individual has overdosed. The method optionally provides for injection of an opioid receptor antagonist into the individual to reverse the effects of the overdose. Also provided is a device for implementing these methods.

31 Claims, 8 Drawing Sheets

(51) Int. Cl.

| | | |
|---|---|---|
| | *A61B 5/11* | (2006.01) |
| | *A61B 5/1455* | (2006.01) |
| | *A61K 31/485* | (2006.01) |
| | *A61M 5/142* | (2006.01) |
| | *A61M 5/145* | (2006.01) |
| | *A61M 5/172* | (2006.01) |
| | *A61M 5/20* | (2006.01) |
| | A61B 5/08 | (2006.01) |
| | A61B 5/024 | (2006.01) |
| | A61B 5/021 | (2006.01) |

(52) U.S. Cl.
CPC .............. *A61B 5/0816* (2013.01); *A61B 5/681* (2013.01); *A61M 2005/206* (2013.01)

(56) References Cited

U.S. PATENT DOCUMENTS

2017/0000416 A1\* 1/2017 EhrenKranz ............ G16H 20/10
2018/0317841 A1\* 11/2018 Novak, Jr. ............ A61M 5/142

\* cited by examiner

METHOD AND DEVICE FOR AUTOMATIC IDENTIFICATION OF AN OPIOID OVERDOSE AND INJECTION OF AN OPIOID RECEPTOR ANTAGONIST

CROSS-REFERENCE TO RELATED APPLICATIONS

The present application claims the benefit of U.S. Provisional Patent Application Ser. No. 62/270,869 filed on Dec. 22, 2015. The content of that application is hereby incorporated by reference in its entirety.

BACKGROUND

Opioid addiction is a debilitating disease that has increased substantially in recent decades. Around 30,000 people die from opioid overdose every year and in 2014 there were more opioid overdose deaths than any other year on record. Due to the morbidity and mortality of opioid use, clinicians have been encouraged to use naloxone, an opioid receptor antagonist, which has been proven to reverse an opioid overdose. Until recently, the administration of this medication was reserved for use by only highly trained professionals such as doctors, nurses and other emergency personnel, however in the last decade, there has been a significant push to have nonmedical individuals administer it to opioid users in need with good results.

Currently there are two naloxone delivery methods that are available to patients to aid in decreasing the risk of opioid overdose. One administers the medication by the intranasal route, and the other is injected intramuscularly or subcutaneously while giving audio instructions to the bystander on proper technique. Both are effective, and have saved numerous lives. However, neither device provides continuous/intermittent monitoring of the patient. In addition, both require the presence of a conscious and caring bystander since they cannot be administered to oneself during an overdose. Continuous or near continuous monitoring is desirable as it would allow the incidence of overdose to be detected relatively early, thereby increasing the odds of successful intervention. Further, given that many opioid users use drugs alone or use with individuals who may not be at their optimum level of functioning, it is desirable to have a device that does not rely on effective execution by another person.

SUMMARY OF THE INVENTION

Exemplary embodiments of the present technology are directed to a method for detecting the need for and providing assistance to an individual suspected of overdosing on an opiate. The method includes measuring one or more physiological parameters of the individual and transmitting an alert if the parameters were to cross a threshold and put the individual in danger. Also included is a device that may be used to carry out the method. The device carries naloxone or other opioid receptor antagonist and is able to administer it at the first signs of overdose. Although reference will be made to naloxone in the description of embodiments of the invention, it should be recognized that the invention is not limited to naloxone and that other opioid receptor antagonists may be substituted without deviating from the intended scope of the invention. By monitoring vital signs of the individual, the device causes an opioid overdose to trigger a cascade of events that leading to a call for help and optionally administration of naloxone and the reversal of the overdose, thus saving the person's life. The device can be worn as a bracelet, anklet, skin patch, or even be inserted into the body thereby allowing constant monitoring of vital signs. The device can be worn also as a ring on a finger, or even attached to a tooth. By monitoring either one or a combination of respiratory rate, heart rate, and/or blood pressure, the device can recognize an overdose, and respond effectively.

An opioid overdose is notable for sedation, reduced breathing rate, peripheral capillary oxygen saturation ($SpO_2$), heart rate, and blood pressure. If untreated, it may lead to reduced oxygenation, cyanosis, organ damage and death. By recognizing it early and intervening with naloxone, morbidity and mortality can be averted. Embodiments of the method and device disclosed of the present disclosure provide for monitoring the vital signs to accomplish this goal. There are many physical changes that may occur during overdose and tracking several physical parameters with multiple sensors provides the most accurate assessment of the state of the patient and reduces false positives while avoiding disastrous false negatives (missing an actual overdose). Significant drops in respiratory rate, $SpO_2$, and heart rate (and/or other physiological data) below a certain threshold triggers the device. This threshold can be based on both an absolute number (such as heart rate less than 50 beats per minute, or respiratory rate less than 5 beats per minute) and a percentage change from the baseline of the individual (pulse reduced by greater than 25% of baseline pulse). See FIG. 2A for a flow chart containing detailed description of the methodology for automatic detection of an opioid overdose.

The device contains a processor that includes a programmed algorithm that may include user assignable parameters. For example, the device may request the age, height and weight of the wearer of the device and the processor may use this information in an algorithm that determines if an overdose is occurring. Once the device recognizes an overdose, a sequence of events causes further algorithms to be run resulting in the transmission of a message to contact(s) informing them of the overdose and providing GPS coordinates of the location of the wearer. Optionally, the device may also cause actuation of mechanical and electrical systems for providing the drug to the overdosing wearer. Because naloxone is an opioid antagonist, it may produce opioid withdrawal in individuals physiologically dependent on opioids. Opioid withdrawal is uncomfortable. The device includes an abort option that gives the conscious individual a chance to disable the naloxone administration in the unlikely event that the device falsely determines the individual to be overdosed.

In embodiments of the invention, when an overdose is recognized, the device responds with an alarm lasting for a short duration (about 20 seconds). This alarm which may comprise a loud sound and/or vibration and/or flashing screen on the device or on a smart phone screen in communication with the device, for example, through a bluetooth connection, allows for the conscious individual to abort the imminent naloxone administration in the event of an unlikely error. The abort option requires the individual to push a switch on one side, and then simultaneously push a switch on another side, e.g., the opposite side or press the flashing screen for a duration of greater than 5-10 seconds. This permits the conscious individual to easily abort the naloxone cascade should it be unwanted, but also prevents inadvertent abortion of the lifesaving injection when it is needed.

The alerting alarm should be of about 20 seconds duration: long enough to give the conscious individual time to respond, but not too long such that risk arise of complications from the overdose prior to the administration of the naloxone.

One manner in which the device may be worn is via a bracelet or anklet. Recent advances in technology have allowed for respiratory rate to be monitored from the extremities such as via a pulse oximeter. A bracelet that monitors respiratory rate, SpO$_2$ and heart rate makes it simple for individuals to receive and wear the device while still benefiting from the life-saving properties and advantages gained over the other previously mentioned naloxone devices. The device is ideally be worn at all times by the individual and should therefore is resistant to water and other elements to the best degree possible. Individuals may need to have clinicians install and remove the device, and may have to follow up periodically to have battery or parts checked and/or naloxone refilled. Individuals will be able to clearly tell that the device had discharged, and thus be aware of the need to report to the nearest emergency room where they could receive further treatment. Following the discharge of the device, individuals will be advised to follow up with their doctors and/or pharmacist who could inspect and either exchange or refill their device as needed. Individuals may also use the device intermittently, i.e, wear it shortly before use of opioid for a period of 4-6 hr.

Other potential forms of the device includes a patch on the skin that both monitors the vital signs and allows for the naloxone administration, or even an implantable device in the body though this would be more invasive. The patch may be worn on the skin and contain many of the same constituents as the bracelet or anklet including a vial (or two) of naloxone, a monitor for measuring vital signs, a battery, and an actuator or pump to deliver the naloxone. The patch can measure vital signs using one of several approaches, including the use of acoustic recordings from the lungs to accurately determine an overdose. The technology has already been established for automatically injecting medication from a patch or other device, and can be accomplished by using a pump propulsion or electrical motor mechanism to move the medication and needle into the tissues. A device placed on the finger is be another potential form, and offers even more advantage in portability. Another form includes attachment of the device onto a tooth or the nasal septum. By placing on the nasal septum, an acoustic monitor could be best implemented for recording breaths and an atomizer could be used to administer the naloxone automatically through the nostrils rather than an injection device.

The device includes a GPS locating capability allowing the location of the wearer of the device to be sent out to the closest emergency EMT service. This is equivalent to calling an ambulance and quick arrival emergency personnel. Given that naloxone may wear off after about 30 minutes, it is important for individuals to be seen as quickly as possible. Further, considering that some individuals may not want this option, an alternative is to alert a previously assigned emergency contact. In this case, following the determination of an overdose and the administration of naloxone, a text message or phone is placed by the device alerting the emergency contact and providing the location of the individual.

A second naloxone vial may be contained within the device or provided for insertion by the user into the device replacing a used vial. This second vial is useful in avoiding any vulnerable gaps between one opioid overdose reversal to the next while individuals wait to have their device refilled or replaced. A second vial would also be useful during an overdose given that sometimes individuals require multiple doses of naloxone.

The device includes a battery for powering the processor and providing constant monitoring of the sensors, and possibly powers the actuator. The battery preferably lasts for duration of at least a month or longer. To assist in battery life, a mechanism could be incorporated to capture energy from normal body movement and convert it to a mode usable by the device. Also, the device may include solar sensors for charging the battery.

The device contains a vial containing a specific volume and concentration of naloxone contained within a syringe inside the wearable device. The needle of the syringe is capped and insulated to prevent accidental exposure. Naloxone is not be delivered and the needle of the syringe does not penetrate any tissues unless the device is triggered by an overdose recognized by the recorder.

The device includes an actuator that manipulates the syringe and needle in order to inject the naloxone into the desirable tissues when a signal is received from the processor. Additionally, a sensor may be included on or within the needle to determine whether the needle has been inserted into the correct tissue depth. For example, a hall effect sensor may be employed for this purpose.

In accordance with one aspect of the present disclosure, a method for detecting the need for providing assistance to an individual suspected of overdosing on an opiate is provided. The method includes the following steps: (a) measuring continuously or intermittently one or more physiological parameters of the individual using a device, (b) triggering an alarm if the level of at least one of the one or more physiological parameters exceeds a threshold level specific to that parameter; (c) continuing the measuring, and if the alarm was interrupted, suspending the alarm for a period of time and determining thereafter whether the level of the at least one of the one or more physiological parameters had returned to the threshold level; (d) triggering the alarm if, after said period of time, the level of the at least one of the one or more physiological parameters had not returned to the respective threshold level; (e) repeating steps (c) and (d) if in step (d) the alarm was interrupted, and if the alarm was not interrupted in either step (d) or (b) within a fixed duration, transmitting a message to one or more contacts (i) to convey that the individual had overdosed on an opiate and (ii) provide GPS coordinates of the individual.

Embodiments of the above method can include one or more of the following features. In one embodiment, the method further includes providing the device, which is worn by the individual and includes a processor containing a memory, a transmitter, and one or more sensors for measuring the one or more physiological parameters of the individual. In one embodiment, (i) data of the one or more physiological parameters measured by the device is transmitted to a smart phone, (ii) determining if the level of the at least one of the one or more physiological parameters exceeds a threshold level specific to said parameter so as to trigger an alarm is performed in the smart phone, (iii) the alarm is aborted by activating a switch on the smart phone, and (iv) the transmitting a message to one or more contacts is performed by the smart phone.

In one embodiment, the one or more physiological parameters include breathing rate, pulse rate, peripheral capillary oxygen saturation (SpO$_2$), temperature, and blood pressure. In another embodiment, the at least one of the one or more physiological parameters is respiratory rate, its threshold being 5 breaths per minute or cessation of breadth for 30-60 seconds or a duration greater than a baseline established for the individual. In yet another embodiment, the at least one of the one or more physiological parameters is peripheral capillary oxygen saturation (SpO$_2$), its threshold being 85% or 10-15 percent decrease below a baseline established for the individual. In a separate embodiment, two physiological parameters are measured, namely, respiratory rate and SpO$_2$, such that the threshold of the former is 5 breaths per minute or cessation of breadth for 30-60 seconds or a duration greater than a baseline established for the individual and that of the latter parameter is 85% or a 10-15 percent decrease below a baseline established for the individual. In one embodiment, the period of time after which it is determined whether the level of the at least one of the one or more physiological parameters had returned to the threshold level is 5 minutes. In one embodiment, the fixed duration is 20 seconds.

In one embodiment of the above method, in step (a), the alarm is triggered if the level of the at least one of the one or more physiological parameters falls and remains below its threshold for greater than a defined time interval. In one embodiment, the at least one physiological parameter is SpO$_2$, its threshold is 85% or a 10-15 percent decrease below a baseline established for the individual, and the defined time interval is between 60 and 90 seconds. In another embodiment, the at least one physiological parameter is respiratory rate, its threshold is 5 breaths per minute or cessation of breadth for 30-60 seconds or a duration greater than a baseline established for the individual.

In yet another embodiment, the at least one physiological parameter is respiratory rate, its threshold is zero breaths per minute, and the defined time interval is 30 seconds. In a further embodiment, the contacts include emergency responders reachable by 9-1-1 and an established network of able and willing carriers of an opiate antidote. The contacts can also include friends, family members or other people known to the individual. In another embodiment, the method further includes transmitting, if the alarm was interrupted, information that the individual may have sleep apnea or chronic obstructive pulmonary disease (COPD). In yet another embodiment, the device further includes a syringe containing an opiate antidote and an actuator for causing injection of the antidote into the individual; and step (e) further includes (i) triggering administration by the device of a first dose of the antidote, (ii) repeating step (c); and (iii) triggering administration by the device of a second dose of the antidote if the level of the at least one of the one or more physiological parameters had not returned to the respective threshold level. In one embodiment, the opiate antidote is naloxone.

In a further embodiment of the above method, the device includes a mode for recording the one or more physiological parameters without triggering an alarm for a period of time, determining a baseline level for any one of the one or more physiological parameters from the recording, and selecting the threshold level for said physiological parameter to be above or below the baseline level by a defined percent point. For example, during this period (e.g., 12-24 hours), the device records, learns, and sets the individual's baseline physiological data including identifying lower threshold SpO$_2$ data and duration of apnea or reduced respiratory rate consistent with conditions such as sleep apnea and COPD. An alarm is not be triggered unless respirations cease for greater than 90 seconds or SpO$_2$ drops below 65% for greater than 30 seconds. In this mode, the device provides a warning, e.g., a flashing red light that blinks to ensure that the user is aware of the altered function. In one embodiment, the method includes exiting this mode if the individual so chooses.

Another aspect of the present disclosure is a wearable device for automatically sensing an opioid overdose of a patient. The device includes: (a) a housing, (b) a strap attached to the housing for securing the device to the patient, (c) one or more sensors within the housing, the sensors being disposed for contact with a skin surface of the patient for measuring one or more physiological parameters of the patient continuously or intermittently; (d) an alarm inside the housing, the alarm operative to provide an audible or vibration signal, (e) two switches on the housing, the switches being activatable by the patient in response to the audible or vibration signal, (f) a transmitter operative to transmit an alert, and (g) a processor. The processor includes instructions stored in a memory: to receive the measured physiological parameters from the one or more sensors and compare each such parameter to a predetermined threshold for said parameter; and to trigger an alarm, if one or more of the thresholds are crossed. The alarm is capable of being aborted. Aborting the alarm requires pressing both switches, and if the alarm is not aborted, the processor instructs transmitting of an alert to one or more contacts. The alert includes providing to the one or more contacts GPS coordinates of the patient and a message indicating that the patient has overdosed on an opiate.

Embodiments of the above device can include one or more of the following features. In one embodiment, the device further comprises an interface for selecting a mode for recording the one or more physiological parameters without triggering an alarm for a period of time, determining a baseline level for any one of the one or more physiological parameters from the recording, and selecting the threshold level for said physiological parameter to be above or below the baseline level by a defined percent point. In one embodiment, the device contains a syringe including a needle inside the housing. The syringe contains an opioid receptor antagonist and an actuator mechanically coupled to the syringe and responsive to an actuation signal from the processor for causing the syringe to inject the opioid receptor antagonist into the patient. If the alarm is not aborted, in addition to transmitting the alert, a first actuation signal is transmitted to the actuator to cause a first injection of the opioid receptor antagonist into the patient. In another embodiment, if after a period of time following the first injection, the physiological parameters have still not returned to the one or more thresholds, a second actuation signal is transmitted to the actuator to cause a second injection of the opioid receptor antagonist. The device can be configured to be worn by the patient on several parts of the body including an ankle, a wrist, a calf, a thigh, or an upper arm. In one embodiment, it is configured to be worn on a wrist. The one or more physiological parameters include respiratory rate, pulse rate, peripheral capillary oxygen saturation (SpO$_2$), temperature, and blood pressure. In one embodiment, the physiological parameters are breathing rate and SpO$_2$. In one embodiment, the opioid receptor antagonist is naloxone. In another embodiment, the switches are on opposite sides. In yet another embodiment, the one or more physiological parameters are measured or derived using pulse oximetry and one of the sensors is a pulse oximeter sensor. In another embodiment, one of the sensors measures blood pressure. In one embodiment, a blood pressure measurement is taken if the respiratory rate falls below a threshold of 5 breaths per minute or there is a cessation of breadth for a duration established for the individual. In another embodiment, the processor instructs the device to press against the skin surface to permit accurate measurement of blood pressure. In another embodiment, prior to injection, the processor instructs the device to press against the skin surface for effectiveness of the injection.

BRIEF DESCRIPTION OF THE DRAWINGS

The foregoing and other features and advantages provided by the present disclosure will be more fully understood from the following description of exemplary embodiments when read together with the accompanying drawings, in which.

DETAILED DESCRIPTION OF THE INVENTION

As used in this description and the accompanying claims, the following terms shall have the meanings indicated, unless the context otherwise requires:

The term "wearable" shall mean the ability of the device to be attached to an individual at all times. The device can be worn in such a manner that it is portable so as to not interfere with or restrict daily activities.

The term "opioid receptor antagonist" shall mean a drug such that binds to the mu opioid receptor and inhibits or reverses the effects of opioid agonists such as heroin or other opioids. For example, the drug is naloxone.

The phrase "exceeds a threshold level" as used herein shall mean that value of the measured parameter at issue goes either above or below the accepted level for that parameter for a healthy individual or the baseline established for the individual for that parameter.

As used herein the phrase "measuring continuously or intermittently" shall mean measuring without any break or with short breaks such as breaks of 10 or 20 seconds.

As used herein, "antidote" shall mean a medicine for counteracting the effects of an opiate.

Figure 1:
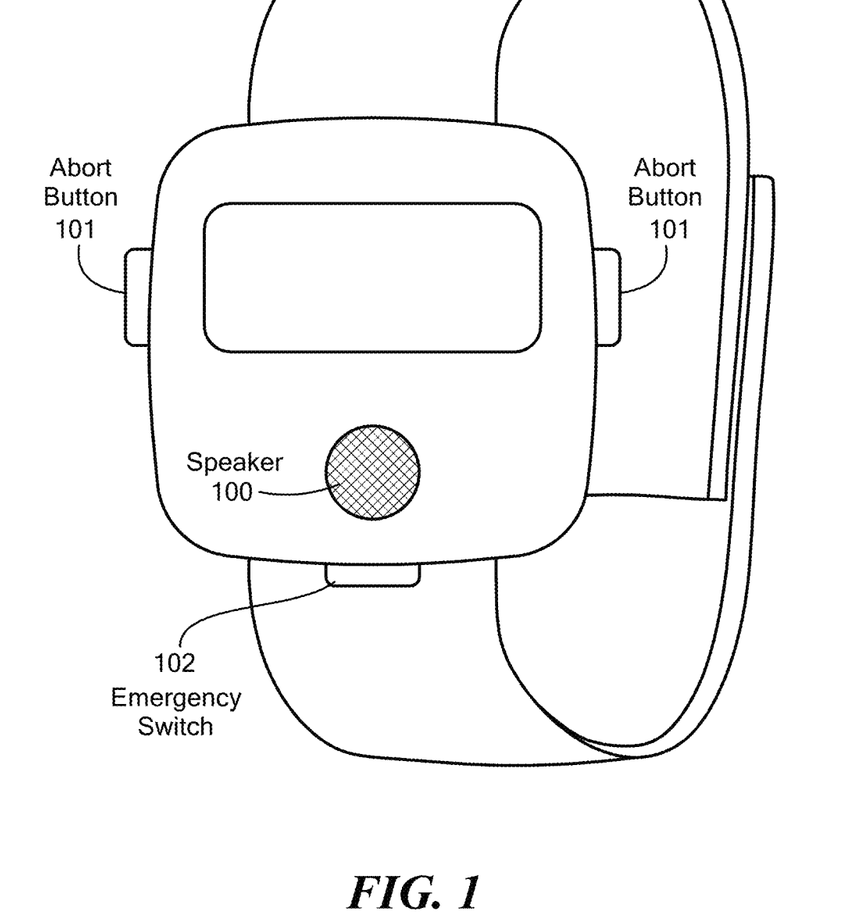
FIG. 1 is a schematic diagram of one embodiment of the device for automatic identification of an opioid overdose and injection of an opioid receptor antagonist described in the present disclosure.

FIG. 1 shows one embodiment of the invention for automatic identification of an opioid overdose and injection of an opioid receptor antagonist. The wearable device, whether a bracelet, anklet, patch, or of some other form is not one that is easily removed. It is close or tight enough on the desired location such that it is able to serve its purpose (i.e. continuous or intermittent monitoring of physiological data, and ability to administer medication safely and effectively). The device has the ability to become further tightened on the desired location, for example, in response to an instruction from the processor to both monitor physiological data and administer medication with greater accuracy. The device is light and compact enough so as not to be a burden or nuisance. It may be made in a variety of color and design options. One option could be to resemble that of a watch so as to not promote any stigma that could be associated with a device designed for opioid users.

The wearable device contains a speaker 100 that emits an alarm, i.e., loud and unpleasant sound shortly prior to the triggering of the opioid receptor antagonist injection in order to warn the wearer of the device about the impending action. The device may also include a vibrator to provide a vibration signal prior to the triggering the injection.

The wearable device has two switches, for example, two buttons 101 on separate sides of the device that can be held by the individual to abort the opioid receptor antagonist injection as a failsafe mechanism in the unlikely event of incorrectly determining an overdose had occurred. Both buttons are required to be activated to abort the injection. This serves the purpose of preventing accidental interruption or prevention of naloxone administration during an actual overdose.

Figure 2:
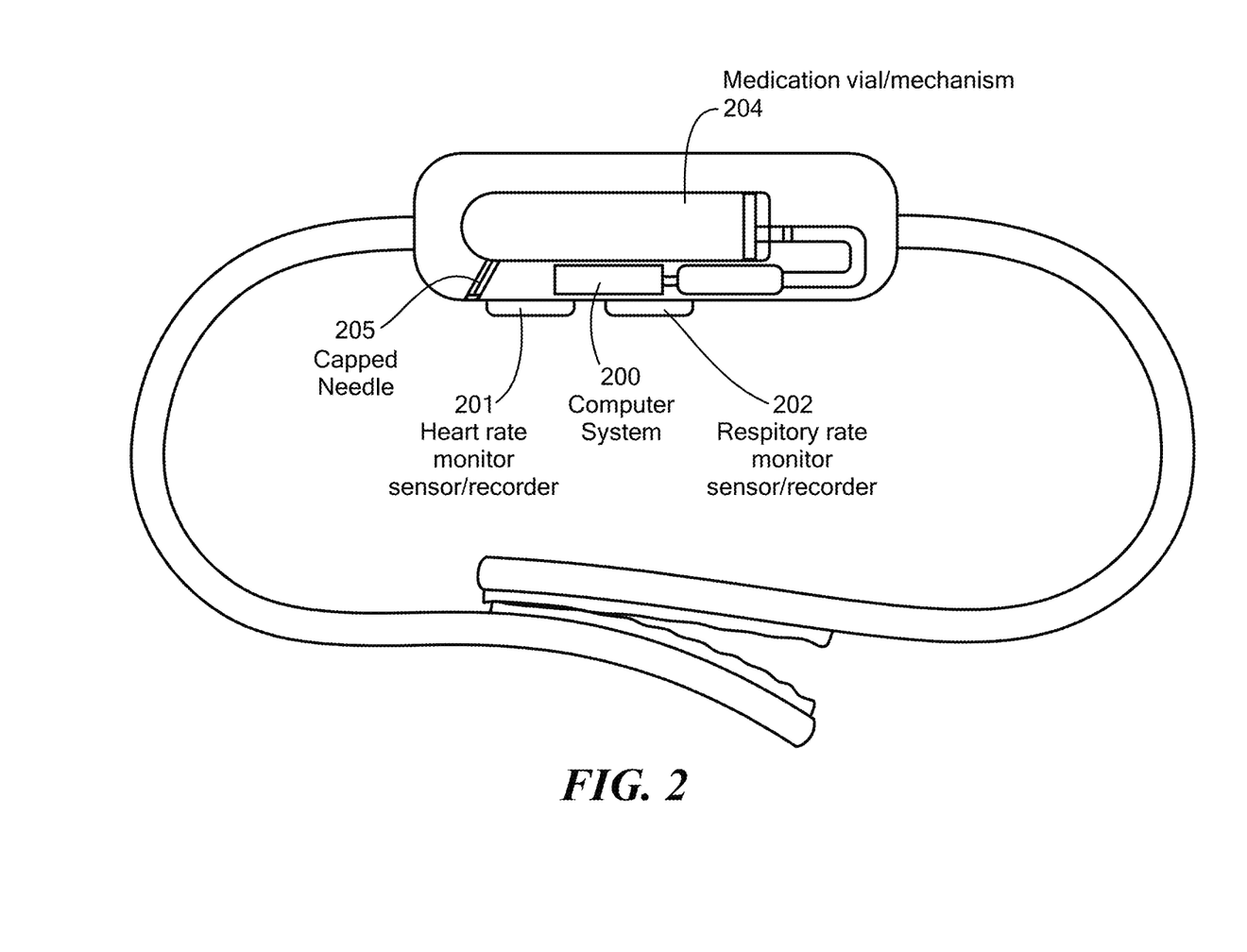
FIG. 2 is a schematic diagram showing a side view of one embodiment of the device of FIG. 1. The device is wearable. Various sensors and electronic and mechanical components included in the device are depicted in this Figure.

FIG. 2 is a side view of the device and shows various sensors and electronic and mechanical components. The device includes a compact data monitor including sensors 201, 202 coupled to a computer system 200 within the wearable device that continuously monitors physiological signs such as pulse, respiratory rate (and/or inspiratory tidal volume), and possibly other signs including blood pressure. Recent scientific advances allows for the monitoring of blood pressure, pulse oximetry, and other physiological signs accurately from the periphery. In different embodiments, this device takes advantage of these capabilities. By monitoring more than one physiological parameter, the device is able to more accurately predict and respond to an overdose. The computer system includes a processor that is programmed with an algorithm designed to determine when an overdose has occurred. It is contemplated that all recording is be done via low power variation sensors to maximize battery power. By using total values and percent change from baseline values, the computer is be able to determine the presence of an overdose. For example, if the pulse drops below 50 beats per minute and is at 25% or greater change from an established baseline, or the respiratory rate drops below 5 breaths per minute for 30-60 seconds, then the threshold for triggering an alarm and activating the actuator to inject the opioid receptor antagonist is met. One of ordinary skill in the art would recognize that other parameters may be used either alone or in combination to determine when an overdose has occurred and the above examples should not be seen as limiting.

Figure 2A:
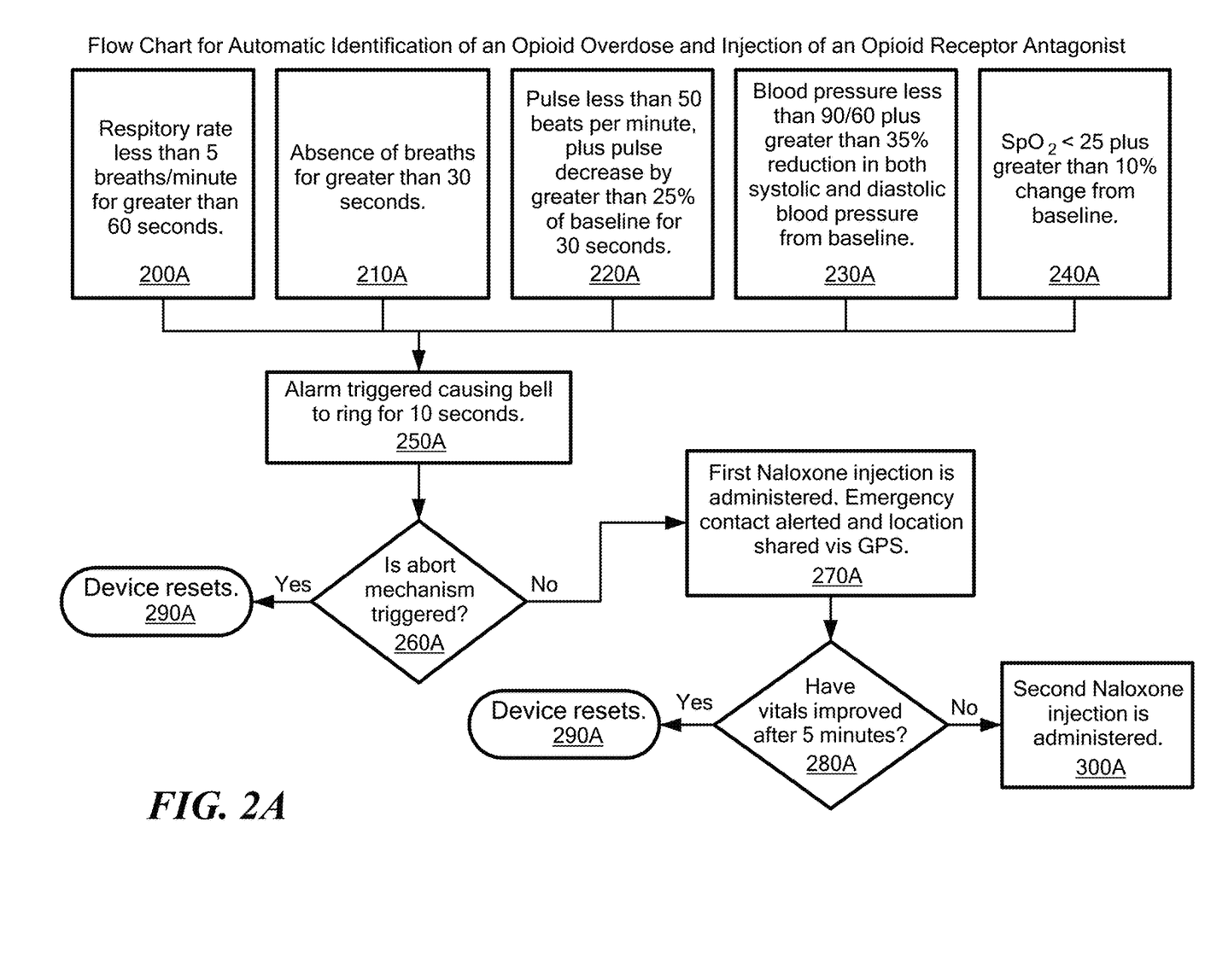
FIG. 2A is an exemplary flow chart showing the methodology for detection of an opioid overdose described in the present disclosure. The flow chart includes steps for activation of an actuator for administration of naloxone.

FIG. 2A. is an exemplary flow chart showing the methodology for detection of an opioid overdose and activation of an actuator for administration of an antidote to the opiate. Should any one of the criteria in the top row of FIG. 2A occur, the process of impending opioid receptor antagonist administration and overdose reversal begins. Significant decrease in respirations 200A, 210A, pulse 220A, blood pressure 230A, or peripheral capillary oxygen saturation (SpO$_2$) 240A are all physiological signs that may be present during an overdose and will trigger this process. Not all of these conditions must be met to trigger the overdose and any one of 200A, 210A, 220A, 230A, and 240A individually may be sufficient to activate the opioid receptor antagonist injection. Also, should more than one occur at once or if all conditions are met simultaneously, the process of impending opioid receptor antagonist administration will be triggered.

As noted in FIG. 2A, once a criterion has been met, and the device recognizes an overdose, then the alarm 250A is triggered. This happens prior to the administration of the opioid receptor antagonist and gives the individual time to abort the injection 260A in the unlikely event of an error. If the individual is conscious (or becomes conscious from a sleeping state) and aborts the injection then the device resets 290A. It then resumes monitoring for any further signs of overdose as noted in 200A, 210A, 220A, 230A, and 240A and begins the cascade should one of them occur again.

In the unlikely event of three abortions within 30 minutes, the device resets for 6 hours permitting the individual to seek medical treatment or assistance to determine the issue and avoid unnecessary disruptions or unnecessary naloxone administration due to a faulty device, medical condition that could mimic overdose, or other reason. Additionally, an individual not using opioids who experienced a false positive would know that overdose was not a factor, and so that individual may consider placing the device into the "reading mode" in attempt to establish a new baseline and improve accuracy of the device.

If the abort mechanism 260A is not triggered within a short time period, for example, 20 seconds or at all, then as the algorithm demonstrates, opioid receptor antagonist shall be administered 270A. Should the device include this feature, emergency contact, e.g., 911 is alerted, and GPS coordinates of the location provided to the contact.

For the 5 minutes after the initial opioid receptor antagonist injection, the device continues to monitor, but no further injections or alarms occurs (280A). If after 5 minutes, no improvement in vital signs occurs, or any of the criteria noted in 200A, 210A, 220A, 230A, and 240A are still met then a second opioid receptor antagonist injection 300A occurs.

If after 5 minutes the vital signs improve, and no longer meet the aforementioned criteria then the device resets, and begins monitoring again 290A.

It should be noted that the flowchart and the suggested time limits and parameters are meant to be exemplary, and that there could be other measures or criteria used in order to maximize safety and accuracy. The device may be equipped to record the preceding 5 or 10 minutes prior to and after the administration of opioid receptor antagonist in order to promote future research and improvement regarding this algorithm. While each individual criterion 200A, 210A, 220A, 230A, or 240A is sufficient to begin to reversal process, less or more strict criteria may prove more useful, and may be used. By combining parameters such as $SpO_2$, low blood pressure and low pulse or low respiratory rate, and requiring that they all be satisfied, the likelihood of false alarms goes down, though the risk of a missed overdose may increase. With regard to monitoring blood pressure, through the use of pulse transit time, an accurate analysis of systolic, diastolic, and mean arterial pressure, can be obtained and used in determining whether an overdose has occurred.

The device also includes an actuator 203. The actuator 203 could be of various designs known to those of ordinary skill in the art for automated injectors of medications. The actuator is in electrical communication with processor 200 and receives signals including a signal to initiate the actuator 203. The actuator 203 may use a propulsion mechanism relying on pressurized air to provide the driving force for administering the naloxone.

Once the computer algorithm operating on the computer processor 200 determines that an overdose has occurred, the actuator repositions a capped or otherwise housed needle 205 such that it is removed from its housing and exposed, and then mobilizes the needle 205 into the patient's tissues while the opioid receptor antagonist is forced into the syringe and out of the needle from a medication vial 204. The medication vial 204 contains sufficient opioid receptor antagonist, e.g., naloxone to reverse a typical opioid overdose. In certain embodiments the dosage may be 0.4 mg naloxone. Given that the locations the device administers the opioid receptor antagonist to includes those that have not previously been used to reverse an overdose (the wrist or ankle for example), it should be understood that a different dose may be optimal for these locations and it may be greater or less than 0.4 mg. The naloxone vial 204 is enclosed in a dark, insulated vial such that is shielded from the elements like sun or harsh temperatures to maintain its effectiveness. In certain embodiments of the invention, the device may contain two vials of opioid receptor antagonist should the portability permit this, and is capable of administering the second vial either during a failed or minimal response to an initial naloxone injection (a few minutes after the first), or to be used at a later date following a successful overdose reversal. The latter example is meant to protect individuals who may still be prone to opioid use while they wait to have their first naloxone vials refilled.

The needle 205 is housed in a sterile cap or similarly covered such that it is not exposed to microbes, and not at risk of accidentally discharging or piercing the individual. The cap of the needle 205 is removed via the actuator 203 during an overdose such that the needle 205 can enter the tissues and administer the opioid receptor antagonist. The needle 205 is short in length so as to not enter too deep into tissues causing unnecessary damage during an overdose reversal. The angle and approach takes into account avoiding major nerves and arteries as which is of less concern for subcutaneous administration, which the device is capable of achieving. The device is also capable of intramuscular administration of the antagonist. The administration of the opioid receptor antagonist can be done using any known administration technology so long as the administration mechanism were of a sufficient force to introduce the opioid receptor antagonist into the tissues. These administration mechanisms may include recently discovered needleless technique that uses high velocity as well as mechanisms by which the wearable tightens prior to administration of the antidote in order to provide sufficient opposing force to effectively administer the antagonist.

Figure 3:
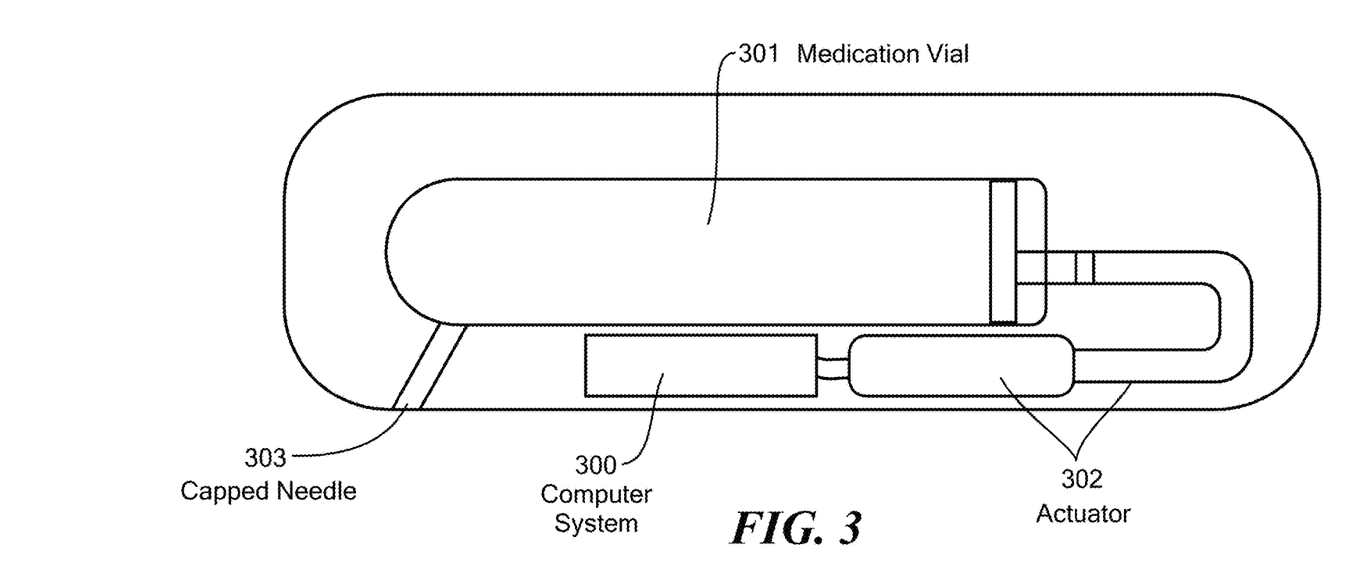
FIG. 3 is a schematic diagram showing an internal view of one embodiment of the device. This view shows a medication vial, actuator, and a capped needle.

FIG. 3 shows an internal view of an embodiment of the invention including a medication vial 301, actuator 302, and a capped needle 303. The medication vial 301 contains an opioid receptor antagonist at a dose and volume sufficient to reverse an opioid overdose. In certain embodiments of the device, a second opioid receptor antagonist vial is accommodated, which can be used in the event a person fails to recover after the first injection, or at a later date prior to the device being switched or reloaded.

Having two vials offers tremendous advantage as there have been many reports of individuals requiring multiple doses of therapeutic amounts of the opioid receptor antagonist naloxone during overdose and also because there is a window of vulnerability where the individual would not possess the safety benefits of the device following its discharge should there be only one antagonist vial. A second active vial enables the individual to be protected while waiting to get a refill following an overdose reversal.

Embodiments of the invention include a computer system or microprocessor 300. The computer system 300 serves the function of processing data from the physiological monitors and deciding when the algorithm for beginning the opioid receptor antagonist cascade is satisfied. Once the algorithm is met, computer system 300 triggers an actuation signal for the actuator 302 to begin administration of the opioid receptor antagonist (after allowing time for aborting the injection). The computer system 300 is lightweight, efficient with low energy needs such that it can be run on limited battery power. The medication vial 301 contains sufficient opioid receptor antagonist to reverse a typical opioid overdose.

Figure 4:
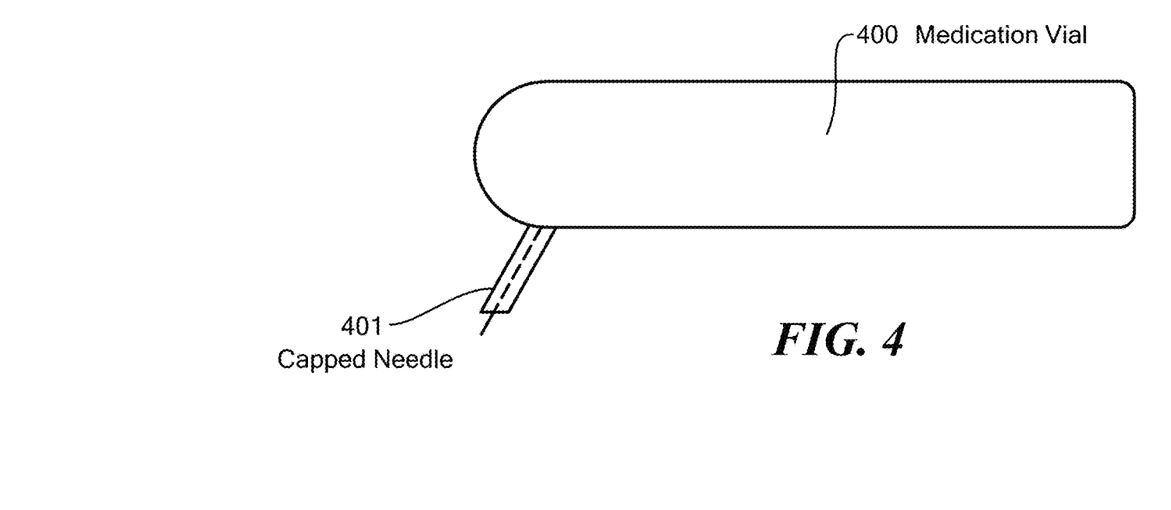
FIG. 4 shows a side view of the medication vial and capped needle shown in FIG. 3.
Figure 4A:
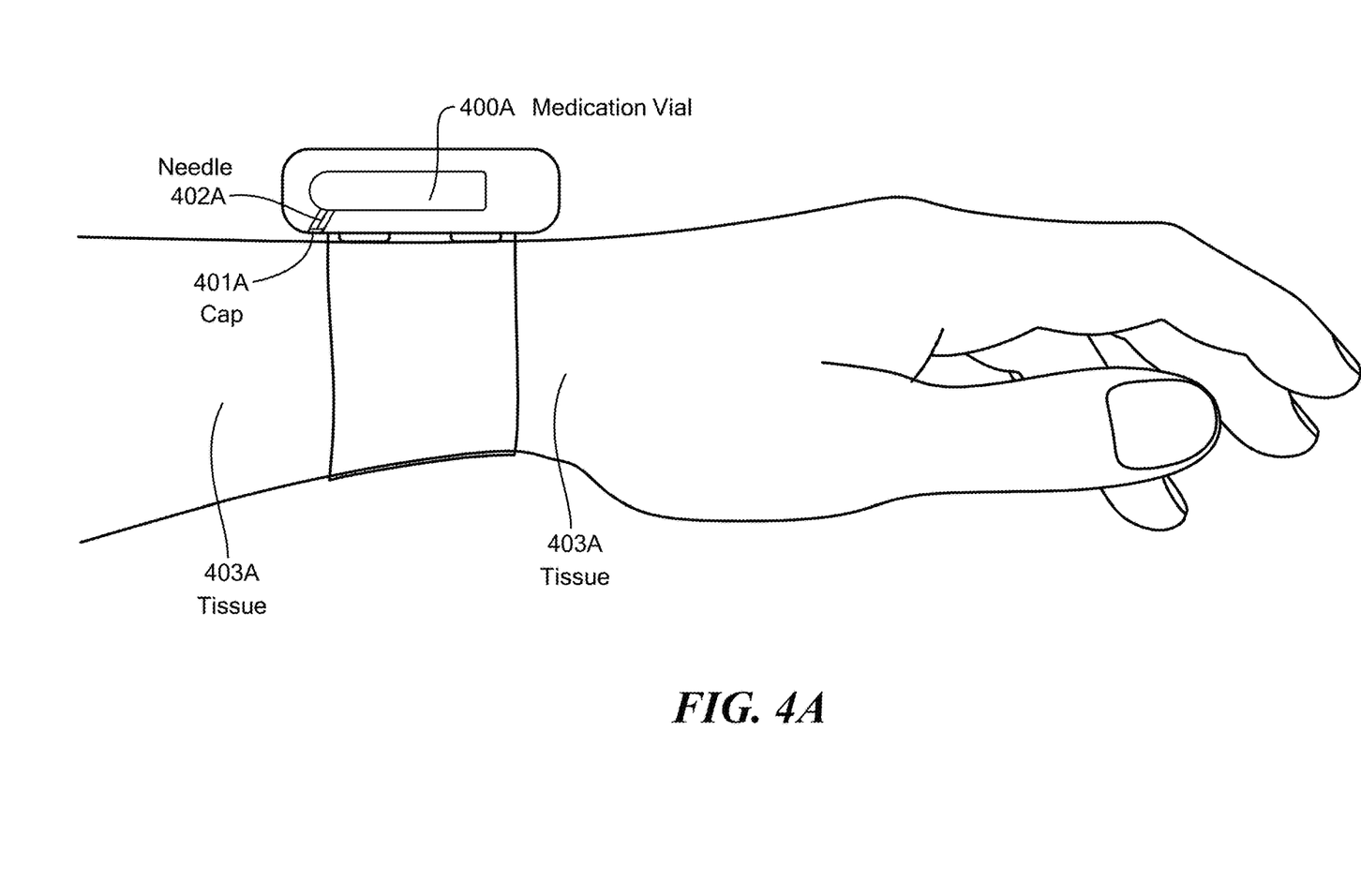
FIGS. 4A-4C show the needle shown in FIG. 3 in different positions, including capped within the housing (4A), uncapped (4B), and inserted into a patient (4C).
Figure 4B:
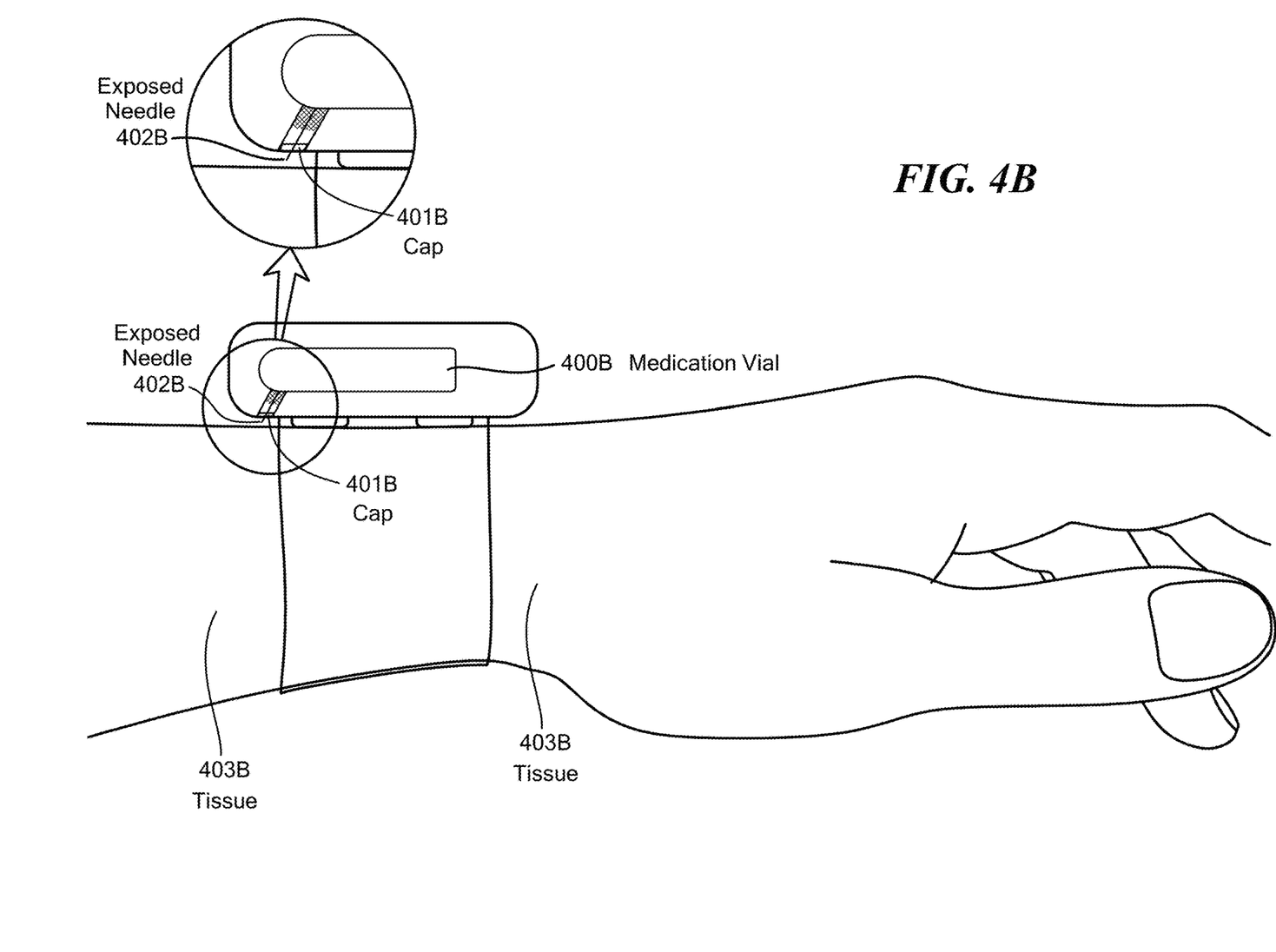
Figure 4C:
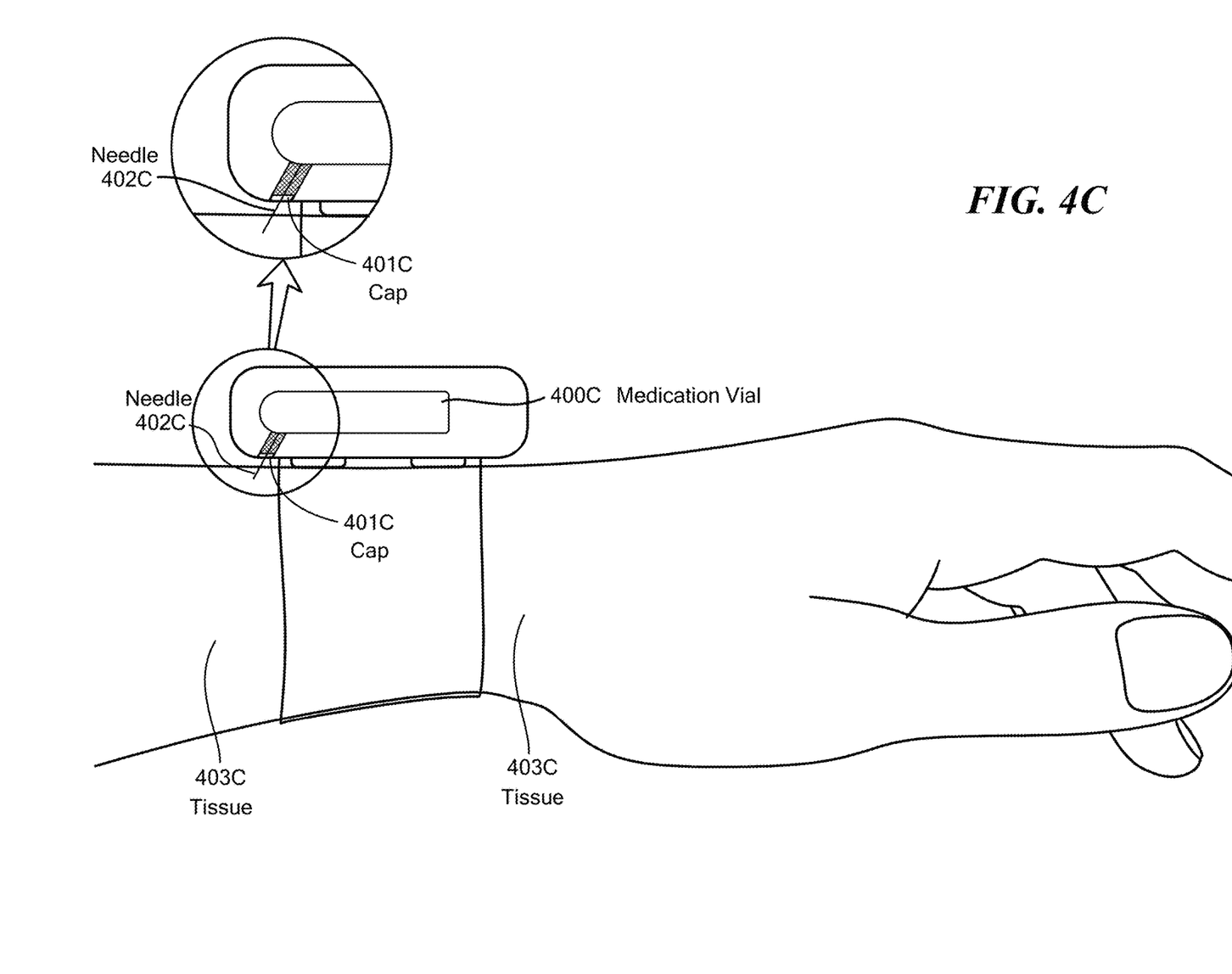

FIG. 4 shows a side view of the medication vial and capped needle. The syringe contains the opioid receptor antagonist vial(s) 400 and the needle and cap 401 and is designed in such a way that administration of the antagonist can be done safely and effectively without the syringe going off accidentally. FIGS. 4A-4C show the medication vial 400A and the capped needle prior to (402A), during (402B), and after (402C) the process of opioid receptor antagonist administration. Prior to the recognition of an overdose, the needle 402A is secured and unexposed within the cap 401A or other housing device. This prevents accidental injection or piercing of tissues 403A. Following the recognition of an overdose, the cap 401B is caused to be pierced or removed and the needle 402B protrudes through the shield and approaches the individual's tissue 403B. Following the needle 402B becoming exposed or protruding through the housing device 401C, it is be driven into the individual's subcutaneous or intramuscular tissue 403C while the actuator expels and delivers the naloxone into the tissue 403C. This may be accomplished by a spring-loaded syringe or other mechanism established by prior auto-injectors currently available. There are numerous auto-injectors available on the market including epi-pens, insulin auto-injectors, the aforementioned naloxone auto-injector, and those for other chronic condition like rheumatoid arthritis or multiple sclerosis. The military also has used auto-injectors for combating exposure to toxins in active duty personnel. It should be noted that many of these auto-injectors rely on the manipulation by an individual. The present disclosure includes an embodiment in which no human manipulation is required. Rather the injection occurs in response to a signal from the microprocessor and actuator. It should be additionally noted that a needleless auto-injection may be used so long as the portability of the device is not sacrificed.

Figure 5:
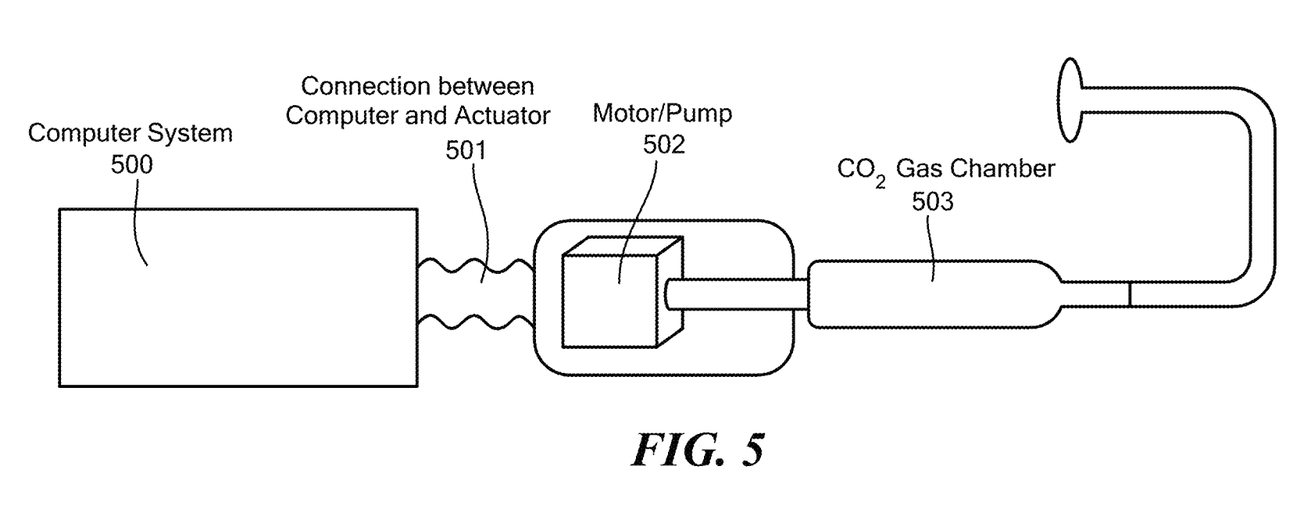
FIG. 5 is a schematic diagram of one embodiment of the device. It depicts the internal components of the device including a motor/pump and a gas chamber for activation.

FIG. 5 shows internal components of a device of the present disclosure including a motor/pump and gas chamber for activation. The actuator serves as a bridge between the computer/monitor 500 and the syringe. It powers the removal of the protective cap from the needle of the syringe, moves the needle and positions it into the appropriate tissues, and then injects the opioid receptor antagonist. This is effectuated via a pump like mechanism. The microprocessor 500 is connected to the actuator via electrical wiring 501 that is insulated and protected from environmental damages. The wiring provides power via the connected battery.

The actuator is be driven by a pump 502, a motor 502, or both. As noted previously the actuator operates via propulsion of air 503 to provide the force necessary to drive the opioid receptor antagonist from the vial through the syringe needle and into the tissues.

Figure 6:
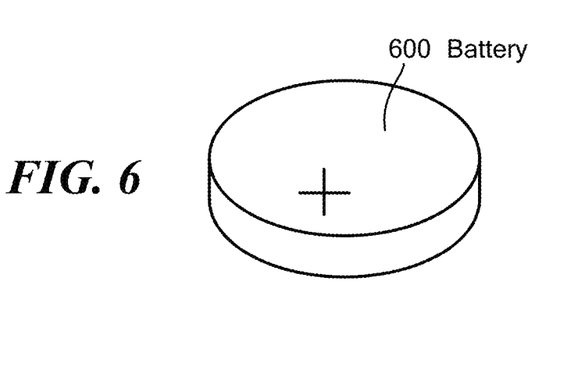
FIG. 6 shows an exemplary battery that may be used to provide power to the electrical components of the device of FIG. 1 including sensors, a processor and an actuator.

FIG. 6 shows an exemplary battery 600 that may be used to provide power to the electrical components of embodiments of the invention including the sensors, processor, and actuator. The battery 600 is small, but powerful enough to maintain appropriate operation of the device for sufficient time. When the battery is low, or should it malfunction, a warning light or some other method of communication appears letting the individual know that the device should be brought in for maintenance.

In one embodiment, the device for automatically sensing an opioid overdose of a patient also includes an interface for selecting a mode ("reading mode") for recording the one or more physiological parameters without triggering an alarm for a period of time. This mode further provides for determining a baseline level for any one of the one or more physiological parameters from the recording and selecting the threshold level for the physiological parameter to be above or below the baseline level by a defined percent point. In the "reading mode" the device asks the user, for example, if the user had used an opioid in the previous 24 hours. The user's answer is be factored into the process for establishing the baseline and thresholds for activating the alarm. This is important given the expectation that opioid, if used, would have lowered $SpO_2$ and breathing efforts of the individual. Therefore, an individual naïve to opioids or who has been free from opioids would be expected to have a more significant drop in $SpO_2$ without triggering overdose, whereas an individual presently or recently on high dose opioids would already be suffering from the effects of the opioids on the respiratory drive, and would have less reserve or cushion. As such, for the latter, the threshold for triggering overdose should be closer to what was recorded to better protect that individual.

Of note, there may be times when an individual is in a situation where he is not overdosing but another opiate user is. In this case, in one embodiment, the individual would be able to place the device on such user so that it could inject the life-saving antidote, with activation, for example, of an emergency switch 102 (See FIG. 1). The device may be made in such a way that it is not easily removed, and can be used in certain clinical situations where a controlled substance is prescribed to a patient by a physician on the condition that the patient wear such device. In this setting, the physician may feel more willing to prescribe the controlled substance if the patient wears the device. The device may have the additional feature of monitoring use of an illicit drug through testing sweat or through other means of testing for the presence of known metabolites, as well as the metabolites of the prescribed drug. This would be a pivotal intervention in addressing adherence to medications prescribed, as well as reduce illicit drug use and diversion of controlled medications and ultimately improve safety and treatment of those with pain or addiction.

In another embodiment the device can include an accelerometer. Data generated by the accelerometer may be used alone or in combination with pulse oximetry and other physiological data to protect individuals prone to seizures as well as those who may have had an accident and become hurt and unconscious so that a friend or 911 could be alerted. With seizures, the rhythmic accelerometer changes may be used to identify seizure when combined with other physiological data and thereby trigger transmission of a message calling for help and optionally sounding of an alarm. Additionally, a large peak in accelerometer data consistent with a fall and slamming of the device could also activate the trigger (which would also be helpful in case of a trauma like car accident or a fall unrelated to seizure). The device would alert a contact in the same manner as if an overdose has occurred. Additionally the user would have an opportunity to abort the call for help or the alarm, if he or she is conscious (which is a cognitive test); otherwise the call for help would be affected.

In one form of use of the device, persons would not routinely wear the device, but would put it on only prior to drug use. In this scenario, persons using recreational or illicit opioids would put on the device prior to use in order to have protection from accidental overdose. In this case the device would provide valuable protection, particularly for someone using alone. However, this would require some planning on the individual's part—namely that the user has the device charged, and brings the device with him or her. This could be problematic given that people often lose, misplace, or forget to wear or charge their wearable devices. It would not be unexpected for this to be more likely in persons actively using opioids given their known effects on cognition and planning.

Additionally, it is worth mentioning that a significant proportion of opioid overdoses do not occur from illicit drugs, but from prescribed opioids. People with chronic pain who take opioids throughout the day are at risk and may not realize what is happening before it is too late. Therefore, there could be tremendous advantage to having people at risk of overdose wear the device at all times. With this approach, there would be minimal need to plan to bring the device as the hope would be that the user would never or rarely remove it. A long-lasting battery, reliability, comfort of wear, and an aesthetically pleasing look are all important features of the device. Implementing known techniques for extending battery life is within the contemplation of the present invention. Additionally the ability to wear the device on the wrist together with a lightweight and non-descript design increases the acceptability of the device.

Further, other medical conditions exist that mimic opioid overdose and as such, a method to distinguish them from opioid overdose is important to reduce false positives. This would prevent frustration in the user, and unnecessary anxiety in friends who receive alerts following overdose. One of the tremendous advantages of this device is that it offers the ability to distinguish opioid overdose from these other conditions, thus greatly improving the reliability, accuracy and function of the device. Over 40 million Americans have some sort of sleep disordered breathing, and 1 in 5 have sleep apnea. Sleep apnea is more common in those with certain medical conditions including drug and alcohol abuse. Those with sleep apnea, have significant periods where their breathing rates are reduced, or stop completely, leading to low blood oxygenation which can mimic overdose. Obstructive sleep apnea, which is the most common form of sleep apnea is easily treatable, and its physiology can be differentiated from opioid overdose by many different parameters. Unlike overdose, with obstructive sleep apnea, there is typically a significant increase in blood pressure and this can be measured to distinguish it from overdose. By measuring blood pressure via photoplethysmography and pulse transit time, or ballistocardiography, the device could reduce false positives and significantly increase user acceptance, permitting continuous, uninterrupted use. Pulse variability could also be factored into this algorithm in order to address this issue. It has been noted that pulse can decrease and then increase during both overdose and obstructive sleep apnea, though the extent and pattern can be quite different in the two conditions, permitting the previously described method/algorithm or similar formulation of it to offer tremendous advantage in differentiating between the two conditions.

In one embodiment the device will include a feature whereby the user can select a "reading mode" that will monitor physiological signs for 12-24 hours in order to better establish the specific physiological changes that occur with the individual. In this setting, the algorithm would be altered once the typical or baseline trends of physiological changes are established. For example a person with sleep apnea who typically has apnea episodes with desaturations reaching 75% range would benefit because the device would record this information, learn and retain it, and then set the required activation or alarm threshold for a percentage below 75%, e.g., 10% below. In this particular instance, the person's data would then activate the device to trigger an alarm if the $SpO_2$ went to 67.5% or below for the required duration. During the "reading mode" the device would not activate unless extreme changes occurred such as respirations cease for greater than 90 seconds or $SpO_2$ drops below 65% for greater than 30 seconds. A red light would blink during this mode alerting the user of the reduced protection at this time.

Chronic obstructive pulmonary disease (COPD) is another condition wherein certain physiological parameters may appear similar to that of overdose, and where the "reading mode" would offer tremendous benefit. Blood oxygenation is reduced significantly in both COPD and overdose, though in COPD respiratory rate does not decrease as severely and may even increase. By pairing respiratory rate and blood oxygenation, the device would solve this issue and prevent false positive responses in those with stable COPD. Additionally the reduced blood oxygenation will occur on a more chronic level unlike with overdose, which will always be acute. Like with apnea, a COPD feature requiring reduction in blood oxygenation from baseline in addition to below the 85% threshold could be available for those with COPD, though this would additionally increase the risk for delayed intervention.

If appropriate treatment for sleep apnea or COPD resulted in improvement of symptoms, the individual should be made aware that a new baseline should be set in "reading mode" to improve the accuracy and function of the device in recognizing and prevention overdose. It is additionally noted that because individuals with sleep apnea are constantly waking up, there may be significant differences in accelerometer data, which could be used in contrast to what occurs with opioid overdose.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, networker, or locator.) Source code may include a series of computer program instructions implemented in any of various programming languages (e.g., an object code, an assembly language, or a high-level language such as FORTRAN, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL.).

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A device for automatically sensing an opioid overdose of an individual, the device being wearable, the device comprising:
    a housing;
    a strap attached to the housing for securing the device to the individual;
    one or more sensors within the housing, the one or more sensors being disposed for contact with a skin surface of the individual for measuring one or more physiological parameters of the individual continuously or intermittently;
    an alarm inside the housing, the alarm operative to provide an audible or vibration signal;
    two switches on the housing, the switches being activatable by the individual in response to the audible or vibration signal;
    a transmitter operative to transmit an alert;
    a processor comprising instructions stored in a memory:
        to receive a measured one or more physiological parameters from the one or more sensors and compare each said measured one or more physiological parameter to a predetermined threshold; and
        to trigger the alarm, if the predetermined threshold for any one of the measured one or more physiological parameters is crossed, wherein (i) the alarm is capable of being aborted, (ii) aborting the alarm requires pressing each of the two switches, and (iii) if the alarm is not aborted, transmitting the alert to one or more contacts, the alert comprising providing to the one or more contacts GPS coordinates of the individual and a message indicating that the individual has overdosed on an opioid; and
    an interface for selecting a mode for recording the one or more physiological parameters without triggering the alarm for a period of time, determining, from the recorded one or more physiological parameters, a baseline level for said each of the recorded one or more physiological parameters, and selecting a new threshold level for said each of the recorded one or more physiological parameters, wherein said new threshold level is above or below the baseline level by a defined percent point.

2. The device of claim 1, further comprising:
    a syringe including a needle inside the housing, the syringe containing an opioid receptor antagonist; and
    an actuator mechanically coupled to the syringe and responsive to an actuation signal from the processor for causing the syringe to inject the opioid receptor antagonist into the individual;
    wherein if the alarm is not aborted, in addition to transmitting the alert, transmitting a first actuation signal to the actuator to cause a first injection of the opioid receptor antagonist into the individual.

3. The device of claim 2, wherein if after a period of time following the first injection, any of the physiological parameters has still not returned to the predetermined threshold, or the new threshold level if the interface is used, transmitting a second actuation signal to the actuator to cause a second injection of the opioid receptor antagonist.

4. The device of claim 2, wherein the opioid receptor antagonist is naloxone.

5. The device of claim 1, configured to be worn by the individual on an ankle, a wrist, a calf, a thigh, or an upper arm.

6. The device of claim 1, configured to be worn by the individual on a wrist.

7. The device of claim 1, wherein the one or more physiological parameters include respiratory rate, pulse rate, peripheral capillary oxygen saturation ($SpO_2$), temperature, and blood pressure.

8. The device of claim 1, wherein the one or more physiological parameters are breathing rate and $SpO_2$.

9. The device of claim 1, wherein the two switches are on opposite sides of the housing.

10. The device of claim 9, wherein the processor instructs the device to press against the skin surface to permit accurate measurement of blood pressure.

11. The device of claim 1, wherein the one or more physiological parameters are measured or derived using pulse oximetry and one of the one or more sensors is a pulse oximeter sensor.

12. The device of claim 1, wherein one of the one or more sensors measures blood pressure.

13. The device of claim 12, wherein a blood pressure measurement is taken if a respiratory rate falls below a threshold of 5 breaths per minute or there is a cessation of breadth for a duration established for the individual.

14. The device of claim 1, wherein the interface is such that the alarm is not triggered during the period of time of the recording the one or more physiological parameters unless respirations cease for greater than 90 seconds or $SpO_2$ drops below 65% for greater than 30 seconds.

15. The device of claim 1, wherein (1) the one or more physiological parameters is respiratory rate and the predetermined threshold is 5 breaths per minute or cessation of breadth for 30-60 seconds, or a duration greater than the new threshold level established for the individual; or (2) the physiological parameter is $SpO_2$ and the new threshold level is 10-15 percent decrease below the baseline level established for the individual for a time interval between 60 and 90 seconds.

16. The device of claim 1, wherein the device is capable of distinguishing the opioid overdose from sleep apnea and/or COPD.

17. The device of claim 16, wherein distinguishing the opioid overdose from sleep apnea and/or COPD comprises monitoring changes in blood oxygenation level and/or respiratory rate.

18. A device for automatically sensing an opioid overdose of an individual, the device being wearable, the device comprising:
   a housing,
   a strap attached to the housing for securing the device to the individual,
   one or more sensors within the housing, the one or more sensors being disposed for contact with a skin surface of the individual for measuring one or more physiological parameters of the individual continuously or intermittently;
   an alarm inside the housing, the alarm operative to provide an audible or vibration signal;
   a transmitter operative to transmit an alert;
   a processor comprising instructions stored in a memory:
      to receive a measured one or more physiological parameters from the one or more sensors and compare each said measured one or more physiological parameter to a predetermined threshold; and
      to trigger the alarm, if the predetermined threshold for any one of the measured one or more physiological parameters is crossed, wherein (i) the alarm is capable of being aborted (ii) if the alarm is not aborted, transmitting the alert to one or more contacts, the alert comprising providing to the one or more contacts GPS coordinates of the individual and a message indicating that the individual has overdosed on an opioid; and
   an interface for selecting a mode for recording the one or more physiological parameters without triggering the alarm for a period of time, determining, from the recorded one or more physiological parameters, a baseline level for each of the recorded one or more physiological parameters, and selecting a new threshold level for each said recorded one or more physiological parameters, wherein said new threshold level is above or below the baseline level by a defined percent point for a defined time interval;
   wherein the device is capable of distinguishing the opioid overdose from sleep apnea and/or COPD.

19. The device of claim 18, wherein distinguishing the opioid overdose from sleep apnea and/or COPD comprises monitoring changes in blood oxygenation level and/or respiratory rate.

20. A method for detecting the need for providing assistance to an individual suspected of overdosing on an opioid, the method comprising,
   (a) measuring continuously or intermittently one or more physiological parameters of the individual using the device of claim 1;
   (b) triggering the alarm if said any one of the measured one or more physiological parameters exceeds the predetermined threshold, or the new threshold level if the interface is used;
   (c) continuing the measuring, and if the alarm is interrupted, suspending the alarm for a period of time following interruption and determining thereafter whether said any one of the measured one or more physiological parameters has returned to the predetermined threshold or the new threshold level;
   (d) triggering the alarm if, after said period of time following the interruption, the any one of the measured one or more physiological parameters had not returned to the predetermined threshold or the new threshold level;
   (e) repeating steps (c) and (d) if in step (d) the alarm is interrupted, and if the alarm is not interrupted in either step (d) or (b) within a fixed duration, transmitting the alert to the one or more contacts (i) to convey that the individual had overdosed on the opiate and (ii) provide the GPS coordinates of the individual.

21. The method of claim 20, wherein (i) data of the measured one or more physiological parameters is transmitted to a smart phone, (ii) determining, using the smart phone, if the any one of the measured one or more physiological parameters exceeds the predetermined threshold or the new threshold level for said measured one or more physiological parameter so as to trigger the alarm, (iii) the alarm is aborted by activating a switch on the smart phone, and (iv) the transmitting the alert to the one or more contacts is performed by the smart phone.

22. The method of claim 20, wherein the one or more physiological parameters include breathing rate, pulse rate, peripheral capillary oxygen saturation ($SpO_2$), temperature, and blood pressure.

23. The method of claim 20, wherein the any one of the measured one or more physiological parameters is respiratory rate, its predetermined threshold being 5 breaths per minute or cessation of breadth for 30-60 seconds or a duration greater than a percent decrease below a baseline established for the individual.

24. The method of claim 20, wherein the any one of the measured one or more physiological parameters is peripheral capillary oxygen saturation ($SpO_2$), its predetermined threshold being 85% or a 10-15 percent decrease below a baseline established for the individual.

25. The method of claim 20, wherein the device further comprises a syringe containing an opiate antidote and an actuator for causing injection of the antidote into the individual; and step (e) further comprises
   (i) triggering an administration by the device of a first dose of the opiate antidote,
   (ii) repeating step (c); and
   (iii) triggering an administration by the device of a second dose of the opiate antidote if said any one of the measured one or more physiological parameters has not returned to the predetermined threshold or said new threshold level for said any one of the measured one or more physiological parameters.

26. The method of claim 25, wherein the opiate antidote is naloxone.

27. A method for detecting the need for providing assistance to an individual suspected of overdosing on an opiate, the method comprising,
(a) measuring continuously or intermittently one or more physiological parameters of the individual using the device of claim 18;
(b) triggering the alarm if said any one of the measured one or more physiological parameters exceeds the predetermined threshold, or the new threshold level if the interface is used;
(c) continuing the measuring, and if the alarm is interrupted, suspending the alarm for a period of time following interruption and determining thereafter whether said any one of the measured one or more physiological parameters has returned to the predetermined threshold or the new threshold level;
(d) triggering the alarm if, after said period of time following the interruption, the any one of the measured one or more physiological parameters has not returned had not returned to the predetermined threshold or the new threshold level;
(e) repeating steps (c) and (d) if in step (d) the alarm is interrupted, and if the alarm is not interrupted in either step (d) or (b) within a fixed duration, transmitting the alert to the one or more contacts (i) to convey that the individual had overdosed on the opiate and (ii) provide the GPS coordinates of the individual.

28. The method of claim 27, wherein (i) data of the measured one or more physiological parameters is transmitted to a smart phone, (ii) determining, using the smart phone, if the any one of the measured one or more physiological parameters exceeds the predetermined threshold or the new threshold level for said measured one or more physiological parameter so as to trigger the alarm, (iii) the alarm is aborted by activating a switch on the smart phone, and (iv) the transmitting the alert to the one or more contacts is performed by the smart phone.

29. The method of claim 27, wherein the one or more physiological parameters are respiratory rate and $SpO_2$, wherein the predetermined threshold of the respiratory rate is 5 breaths per minute or cessation of breadth for 30-60 seconds or a duration greater than an established baseline for the respiratory rate and that of the $SpO_2$ is 85% or a 10-15 percent decrease below an established baseline for the $SpO_2$.

30. The method of claim 27, wherein the device further comprises a syringe containing an opiate antidote and an actuator for causing injection of the antidote into the individual; and step (e) further comprises
(i) triggering an administration by the device of a first dose of the opiate antidote,
(ii) repeating step (c); and
(iii) triggering an administration by the device of a second dose of the opiate antidote if said any one of the measured one or more physiological parameters has not returned to the predetermined threshold or said new threshold level for said any one of the measured one or more physiological parameters.

31. The method of claim 30, wherein the opiate antidote is naloxone.

* * * * *